(12) United States Patent
Woge et al.

(10) Patent No.: US 12,090,107 B2
(45) Date of Patent: Sep. 17, 2024

(54) CONTROL OF AN ACTIVE ORTHOTIC DEVICE

(71) Applicant: TENDO AB, Lund (SE)

(72) Inventors: Sofie Woge, Lund (SE); Robin Gustafsson, Lund (SE); Pontus Renmarker, Malmo (SE); Sarawut Kaewwiset Kopfer, Middelfart (DK)

(73) Assignee: TENDO AB, Lund (SE)

( * ) Notice: Subject to any disclaimer, the term of this patent is extended or adjusted under 35 U.S.C. 154(b) by 237 days.

(21) Appl. No.: 17/296,960

(22) PCT Filed: Dec. 7, 2019

(86) PCT No.: PCT/SE2019/051248
§ 371 (c)(1),
(2) Date: May 25, 2021

(87) PCT Pub. No.: WO2020/122792
PCT Pub. Date: Jun. 18, 2020

(65) Prior Publication Data
US 2022/0023133 A1    Jan. 27, 2022

(30) Foreign Application Priority Data
Dec. 12, 2018   (SE) .................................. 1851567-6

(51) Int. Cl.
*A61H 1/02*      (2006.01)
*A61F 5/01*      (2006.01)

(52) U.S. Cl.
CPC ........... *A61H 1/0288* (2013.01); *A61F 5/013* (2013.01); *A61H 2201/1638* (2013.01);
(Continued)

(58) Field of Classification Search
CPC .......... A61H 1/0288; A61H 2201/1638; A61H 2201/165; A61H 2201/5007;
(Continued)

(56) References Cited

U.S. PATENT DOCUMENTS 5,172,551 A   12/1992  Nakajima
5,254,078 A * 10/1993  Carter .................... A61F 5/013
                                                       602/21
(Continued)

FOREIGN PATENT DOCUMENTS

EP       2417941 A1    2/2012
EP       3288721 B1    7/2019
(Continued)

OTHER PUBLICATIONS

Supplementary European Search Report from corresponding European Application No. 19896860, mailed on Jul. 29, 2022; 2 pages.
(Continued)

*Primary Examiner* — Margaret M Luarca
*Assistant Examiner* — Tyler A Raubenstraw
(74) *Attorney, Agent, or Firm* — Tucker Ellis LLP (57) ABSTRACT

An active orthotic device, e.g. a hand orthosis, is attached to one or more limbs of a human subject and comprises a respective set of actuators (21) for moving a respective limb (1A) among the one or more limbs. A method for controlling the orthotic device comprises obtaining one or more bioelectric signals, [S(t)], from one or more bioelectric sensors (10) attached to or implanted in the human subject; processing the one or more bioelectric signals, [5(t)j, for prediction of an intended application force, FA(t), of the respective limb (1A) onto an object; obtaining a force signal, PA(t), from a force sensing device (22) associated with the respective set of actuators (21) and/or the respective limb (1A); and generating, as a function of a momentary difference, e(t),
(Continued)

between the intended application force, FA(t), and the force signal, PA(t), a respective set of control signals, it(t), for the respective set of actuators (21).

17 Claims, 4 Drawing Sheets

(52) U.S. Cl.
CPC .................. *A61H 2201/165* (2013.01); *A61H 2201/5007* (2013.01); *A61H 2201/5061* (2013.01); *A61H 2201/5064* (2013.01); *A61H 2201/5084* (2013.01); *A61H 2230/605* (2013.01)

(58) Field of Classification Search
CPC .... A61H 2201/5064; A61H 2201/5084; A61H 2201/5061; A61H 2230/605; A61H 1/02; A61F 5/013; A61F 2002/6827; B25J 9/0006; B25J 13/00; B25J 13/085
See application file for complete search history.

(56) References Cited

U.S. PATENT DOCUMENTS

| | | | | |
|---|---|---|---|---|
| 5,778,449 | A * | 7/1998 | Oetting | A41D 13/088 2/161.1 |
| 5,800,561 | A | 9/1998 | Rodriguez | |
| 7,396,337 | B2 * | 7/2008 | McBean | A61F 2/72 601/24 |
| 8,998,831 | B2 * | 4/2015 | Sankai | A61H 1/0288 601/40 |
| 9,299,230 | B2 * | 3/2016 | Aviles | G08B 6/00 |
| 9,387,112 | B2 | 7/2016 | Bryant | |
| 9,717,607 | B1 * | 8/2017 | Bostick | A61F 2/54 |
| 10,449,677 | B1 * | 10/2019 | Al Najjar | B25J 9/0006 |
| 2006/0128538 | A1 * | 6/2006 | Sato | A63B 21/00076 482/112 |
| 2010/0041521 | A1 * | 2/2010 | Ingvast | B25J 9/0006 482/49 |
| 2010/0069798 | A1 * | 3/2010 | Cheng | A61H 1/0262 602/5 |
| 2010/0268351 | A1 | 10/2010 | Van Der Merwe | |
| 2011/0060231 | A1 * | 3/2011 | Sato | A63B 71/0622 600/500 |
| 2012/0179075 | A1 * | 7/2012 | Perry | B25J 9/0006 601/33 |
| 2012/0330198 | A1 | 12/2012 | Pataglu | |
| 2013/0072836 | A1 * | 3/2013 | Heaton | A61H 1/0288 601/152 |
| 2013/0226350 | A1 * | 8/2013 | Bergelin | A61H 1/0288 2/160 |
| 2013/0303951 | A1 * | 11/2013 | Liu | A63B 23/16 601/46 |
| 2014/0142470 | A1 * | 5/2014 | Elia | A63B 21/4019 601/5 |
| 2014/0171838 | A1 * | 6/2014 | Aleksov | A61H 3/00 601/33 |
| 2014/0243721 | A1 * | 8/2014 | Bryant | A61F 5/013 602/21 |
| 2014/0277739 | A1 | 9/2014 | Kornbluh | |
| 2015/0112448 | A1 | 4/2015 | Scott | |
| 2015/0148728 | A1 | 5/2015 | Sallum | |
| 2015/0374575 | A1 * | 12/2015 | Kamper | A61F 5/013 601/40 |
| 2016/0242986 | A1 * | 8/2016 | Nagata | A61H 3/00 |
| 2016/0242987 | A1 * | 8/2016 | Nagata | A61H 1/0277 |
| 2016/0259417 | A1 | 9/2016 | Gu | |
| 2016/0287422 | A1 * | 10/2016 | Kelly | A61F 5/0127 |
| 2016/0291731 | A1 | 10/2016 | Liu | |
| 2017/0042704 | A1 * | 2/2017 | Ryu | A61F 2/583 |
| 2017/0049657 | A1 * | 2/2017 | Cortez | A61F 5/0118 |
| 2017/0119553 | A1 * | 5/2017 | Cipriani | A61F 2/76 |
| 2017/0119614 | A1 * | 5/2017 | Yeow | A61H 1/0288 |
| 2017/0235484 | A1 | 8/2017 | Griffin | |
| 2017/0266075 | A1 * | 9/2017 | Becchi | A63B 23/16 |
| 2018/0116310 | A1 * | 5/2018 | Ingvast | B25J 9/0006 |
| 2018/0303698 | A1 * | 10/2018 | Wijesundara | F15B 15/10 |
| 2019/0038222 | A1 * | 2/2019 | Krimon | A61B 5/1107 |
| 2019/0091091 | A1 * | 3/2019 | Park | A61H 1/0288 |
| 2019/0282442 | A1 * | 9/2019 | Muench | A61H 23/0245 |
| 2019/0311648 | A1 * | 10/2019 | Alshami | G09B 5/04 |
| 2019/0343707 | A1 * | 11/2019 | Riener | A61H 1/0244 |
| 2019/0350794 | A1 * | 11/2019 | Angold | A61H 1/0277 |
| 2019/0380857 | A1 * | 12/2019 | Gelanyi | B25J 9/1085 |
| 2020/0170547 | A1 * | 6/2020 | Bai | B25J 9/1694 |

FOREIGN PATENT DOCUMENTS

| | | |
|---|---|---|
| JP | H05111881 A | 5/1993 |
| JP | 2018519004 A | 7/2018 |
| WO | 2016146960 A1 | 9/2016 |
| WO | 2016166588 A1 | 10/2016 |
| WO | 2018050191 A1 | 3/2018 |
| WO | 2018/138537 A1 | 8/2018 |

OTHER PUBLICATIONS

International Search Report and Written Opinion from corresponding International Application No. PCT/SE2019/051248, Feb. 6, 2020, 11 pages.

Nan Li, et al., "Hand Motion Recognition Based on Pressure Distribution Maps and LS-SVM," 2014 International Conference on Mechatronics and Control (ICMC), Jul. 3-5, 2014, 5 pages.

Zhen Gang Xiao, et al., "Control an Exoskeleton for Forearm Rotation Using FMG," 2014 5th IEEE RAS & EMBS International Conference on Biomedical Robotics and Biomechatronics (BioRob), Aug. 12-15, 2014, 6 pages.

Swedish Search Report from corresponding Swedish Application No. 1851567-6, Jun. 25, 2019, 3 pages.

Jakob R. Mathiesen, et al., "Prediction of grasping force based on features of surface and intramuscular EMG," 7th semester conference paper, Aalborg University, Denmark, Group ST773, 2010, 9 pages.

Decision to Grant from corresponding Japanese Application No. 2021-533708, mailed on Feb. 19, 2024; 6 pages with translation.

* cited by examiner

CONTROL OF AN ACTIVE ORTHOTIC DEVICE

TECHNICAL FIELD

The present invention relates to the field of orthotic devices, and in particular to a technique for controlling an active orthotic device.

BACKGROUND ART

An orthotic device is an externally applied device that is designed and fitted to the body of an individual to modify structural and functional characteristics of the neuromuscular and skeletal system. One class of orthotic devices are electromechanical devices that are powered and controlled by a microprocessor or the like for the purpose of augmenting or assisting motor activities of the individual. This type of orthotic device is also known as an active orthosis or exoskeleton.

Active orthotic devices may be used for restoring or at least improving the motor activity of an individual that has fully or partly lost the ability to move one or more limbs or coordinate the movement of two or more limbs, e.g. as a result of an injury, a neuromuscular disease or disorder, functional weakness, or a congenital disorder. For example, there are so-called upper-limb (or upper extremity) orthotic devices, which are applied externally to the arm and/or hand, or segments thereof, and lower-limb orthotic devices for movement assistance in locomotion-related tasks.

An active orthotic device comprises a number of actuators which are operable to impart a movement to one or more limbs. For example, the actuators may include servomotors, e.g. as exemplified in US2015/0148728, a gas actuated piston, e.g. as exemplified in U.S. Pat. No. 5,800,561, a combination of artificial tendons and electric motors, e.g. as exemplified in US2010/0041521, or a shape memory material for selective heating, e.g. as exemplified in U.S. Pat. No. 9,387,112 and WO2018/138537.

If the individual has sufficient neurological activity coupled to the limb(s), the active orthotic device may be controlled based on bioelectric signals from one or more bioelectric sensors that are arranged to detect the electrical activity of relevant muscles.

Such bioelectric sensors include so-called electromyography (EMG) sensors, which may be implanted (intramuscular electromyography, iEMG) or applied to the skin of the individual (surface electromyography, sEMG). An EMG sensor detects the electric potential generated by muscle cells when these cells are electrically or neurologically activated. Thus, a control device for an active orthotic device may be configured to infer the intended movement of a limb based on the wearer's activation of relevant muscle cells.

WO2018/050191 proposes to infer the intention of a wearer of an active exoskeleton based on force sensors (FSRs) rather than bioelectric sensors. The FSRs are mounted around an upper limb to measure radially directed muscle pressure. Force signals from the FSRs are processed by a machine learning algorithm to detect the human intention with respect to both motion and force of an arm or leg. A controller for the exoskeleton receives a reference torque from the machine learning algorithm and generates a reference velocity as input to a feedback loop for velocity control. A control signal for the exoskeleton is generated based on an error signal which is computed as a difference between a reference velocity and a measured feedback value.

Current active orthotic devices suffer from an inability to properly mimic the movement of a healthy individual. It is generally difficult to operate the actuators of the orthotic device to impart a natural movement to the limbs. This is particularly noticeable when the limbs should interact with an external object, e.g. when the orthotic device is arranged on a hand to operate two or more fingers to grip an object. From the wearer's perspective, such a hand orthosis should provide the wearer with the ability to safely pinch, grab and release objects during daily living activities.

SUMMARY

It is an objective of the invention to at least partly overcome one or more limitations of the prior art.

A further objective is to provide a technique of controlling an active orthotic device with improved correspondence to the intention of the wearer.

One or more of these objectives, as well as further objectives that may appear from the description below, are at least partly achieved by a method of controlling an orthotic device, a computer-readable medium, a control device for an active orthotic device, and an active orthotic device according to the independent claims, embodiments thereof being defined by the dependent claims.

A first aspect of the invention is a method of controlling an active orthotic device attached to one or more limbs of a human subject. The active orthotic device comprises a respective set of actuators for moving a respective limb among the one or more limbs. The method comprises: obtaining one or more bioelectric signals from one or more bioelectric sensors attached to or implanted in the human subject; processing the one or more bioelectric signals for prediction of an intended application force of the respective limb onto an object; obtaining a force signal from a force sensing device associated with the respective set of actuators and/or the respective limb; and generating, as a function of a momentary difference between the intended application force and the force signal, a respective set of control signals for the respective set of actuators.

The first aspect enables an active orthotic device to be controlled to actuate one or more limbs based on bioelectric signals that are detected on or in the wearer. The first aspect is based on the insight that an improved correspondence between the intention of the wearer and the resulting movement of the limb(s) by the orthotic device in relation to an object may be achieved by determining the intended application force of the wearer and by controlling the orthotic device accordingly. Specifically, it has been found that the ability of the orthotic device to effect a well-controlled interaction between the limb(s) and the object is achieved by controlling the set of actuators for the respective limb based on the momentary difference between an intended application force and a force signal that represents measured (actual) application force for the respective limb. The force signal is provided by a force sensing device, which may be included in the orthotic device. According to the first aspect, the intended force is determined based on the bioelectric signal(s), which allows the orthotic device to be intuitively and automatically controlled in accordance with the intention of the wearer.

The force sensing device may be of any type and may measure the actual application force directly or indirectly. The actual application force may be the total force applied by a limb onto an object or the force provided to the limb by the orthotic device. Thus, the actual application force at least represents the force provided to the limb by the orthotic device, via the set of actuators, and may optionally also include the muscular force applied by the wearer to the limb. In one example, the force sensing device is a force or strain sensor which is arranged on the limb to measure contact force between the limb and the object. In another example, the force sensing device is a force or strain sensor arranged in the actuator to measure a force that corresponds to or represents the application force. In yet another example, the force sensing device may be a calculation module, which is implemented in software and/or hardware to compute the application force based on a measured orientation/position of one or more moveable elements in the actuator, e.g. a drive axis, a gear, a spring, etc.

The movement of the respective limb is effected by a set of actuators, which operates in accordance with a set of control signals. As used herein, each limb that is controlled by the orthotic device is considered to be associated with a respective set of actuators for imparting a movement to the limb, even if it is conceivable that one actuator is arranged to impart a movement to two limbs (or more limbs). In such an embodiment, each such actuator is considered to be included in two sets of actuators, one for each of the two limbs. Thus, different sets of actuators may overlap with respect to the included actuator(s).

The respective set of actuators may be of any type and may include a servomotor, a DC motor, a pneumatic actuator, a rotary motor, a linear motor, shape memory alloy, conductive polymers, electroactive polymers, electrostatic devices, and combinations thereof. Different types of actuators may be used for different movements and/or for different limbs. When actuated by the set of control signals, the set of actuators convert potential energy (e.g., electrical, compressed gas, fluid pressure, etc.) as supplied by a power source into mechanical energy. The mechanical energy may be transferred to the limb in any way, e.g. by artificial tendons, gears, hinges, etc.

In the following, various embodiments of the first aspect are defined. These embodiments provide at least some of the technical effects and advantages described in the foregoing, as well as additional technical effects and advantages as readily understood by the skilled person, e.g. in view of the following detailed description.

In one embodiment, the method further comprises: determining an intended limb movement for the respective limb, wherein the respective set of control signals is further generated as a function of the intended limb movement.

In one embodiment, the method further comprises: identifying one or more selected actuators among the respective set of actuators based on the intended limb movement for the respective limb, and generating the respective set of control signals for the one or more selected actuators.

In one embodiment, the respective set of control signals is generated to cause the respective limb to perform the intended limb movement and apply the intended application force.

In one embodiment, the intended limb movement is determined among at least two predefined limb movements, and each of the predefined limb movements corresponds to a predefined movement trajectory of the respective limb.

In one embodiment, one of the predefined limb movements corresponds to a predefined movement trajectory in which the respective limb is in a relaxed and/or stationary state.

In one embodiment, the intended limb movement is determined collectively for two or more limbs of the human subject.

In one embodiment, said determining the intended limb movement comprises: processing the one or more bioelectric signals by a pattern recognition algorithm.

In one embodiment, the method further comprises: extracting signal features from the one or more bioelectric signals, and operating the pattern recognition algorithm on input values comprising the signal features, to cause the pattern recognition algorithm to process the input values for determination of the intended limb movement of the respective limb.

In one embodiment, the pattern recognition algorithm outputs at least one candidate limb movement for the respective limb, and said determining the intended limb movement further comprises: validating the at least one candidate limb movement against a position signal representing actual movement of the respective limb.

In one embodiment, the method further comprises: determining a force value from the force signal, and providing the force value as a further input value for the pattern recognition algorithm.

In one embodiment, the method further comprises: obtaining an inertial signal from an inertial sensor in the active orthotic device or on the human subject, determining an inertial value from the inertial signal, and providing the inertial value as a further input value for the pattern recognition algorithm.

In one embodiment, the method further comprises: obtaining a respective position signal from a respective position sensing device associated with the respective set of actuators and/or the respective limb, determining a position value from the respective position signal, the position value being indicative of a momentary position of the respective limb, and providing the position value as a further input value for the pattern recognition algorithm.

In one embodiment, the pattern recognition algorithm comprises an artificial neural network, which is trained to process the input values for determination of the intended limb movement of the respective limb.

In one embodiment, the method further comprises: the artificial neural network has an output layer configured to provide output data indicative of the intended limb movement, said method further comprising: obtaining a respective position signal representing actual movement of the respective limb, and modifying one or more weight factors of the output layer as a function of the respective position signal.

In one embodiment, the method further comprises: obtaining an inertial signal from an inertial sensor in the active orthotic device or on the human subject, processing the inertial signal for detection of a disturbance condition, and, when detecting the disturbance condition, disabling at least the step of generating the respective set of control signals.

In one embodiment, the respective limb is a finger on a hand of the human subject.

In one embodiment, the respective limb is a respective finger on a hand of the human subject, and the intended limb movement corresponds to an intended grip to be formed by one or more fingers on the hand.

A second aspect of the invention is a computer-readable medium comprising computer instructions which, when executed by a processor, cause the processor to perform the method of the first aspect and any of its embodiments.

A third aspect is a control device for an active orthotic device attached to one or more limbs of a human subject. The active orthotic device comprises a respective set of actuators for moving a respective limb among the one or more limbs, and the control device is configured to perform the method of the first aspect or any of its embodiments.

A fourth aspect of the invention is an active orthotic device configured to be attached to one or more limbs of a human subject. The active orthotic device comprises a respective set of actuators for moving a respective limb among the one or more limbs, and the control device of the third aspect.

Still other objectives, features, embodiments, aspects and advantages of the present invention may appear from the following detailed description, from the attached claims as well as from the drawings.

BRIEF DESCRIPTION OF THE DRAWINGS

Embodiments of the invention will now be described in more detail with reference to the accompanying drawings.

DETAILED DESCRIPTION OF EXAMPLE EMBODIMENTS

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more", even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention. As used herein, a "set" of items is intended to imply a provision of one or more items.

As used herein, an "orthotic device" or "orthosis" refers to an externally applied device that is designed and fitted to the body of an individual to modify structural and functional characteristics of the neuromuscular and skeletal system. The wearer of the orthosis may be incapable of moving one or more limbs or may have an impaired ability to control or effect the movement of one or more limbs. The orthosis may thus be arranged to perform, stabilize or assist a movement of one or more limbs, and well as to enhance the force by which a limb interacts with an object. The orthosis may be configured for any limbs or combinations of limbs, including but not limited to any upper body extremity such as an upper arm, a forearm, a hand, a finger, a phalange, or any lower body extremity such as a thigh, a lower leg, a foot, a toe or a phalange. Each such limb is moved in relation to one or more joints, such as a shoulder joint, an elbow joint, a wrist, finger joint, a hip joint, a knee joint, an ankle or a toe joint.

In the following, the orthotic device will be exemplified as a hand orthosis, which is configured to be worn on the hand of an individual and is operable to impart a controlled limb movement to one or more fingers. In the context of a hand orthosis, such a controlled limb movement for one or more limbs may be referred to as a "grip". The hand orthosis may perform, stabilize or assist a grip involving one or more fingers and/or strengthen a grip in contact with an object.

Figure 1:
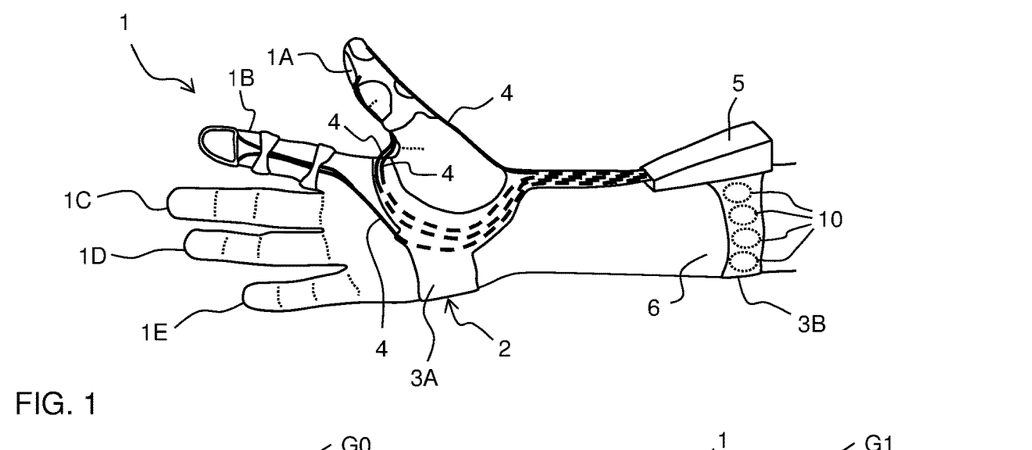
FIG. 1 is a schematic view of an active orthosis arranged on the hand of a human subject.

FIG. 1 is a perspective view of a hand 1 wearing an example orthosis 2 which comprises a cover or sheath 3A configured as a finger glove. The sheath 3A is arranged on the thumb 1A and the index finger 1B and in engagement with the palm and the back of the hand of the individual. In this example, the orthosis 2 is configured to impart a controlled movement to each of the fingers 1A, 1B. Although not shown in FIG. 1, the sheath 3A may also, or alternatively, be configured to be worn on any one of the middle finger 1C, the ring finger 1D and the little finger 1E, and the orthosis 2 may be configured for movement control of any one the fingers 1A-1E or any combination thereof.

In the illustrated example, the hand orthosis 2 comprises cords or lines that serve as artificial tendons 4. The tendons 4 are fastened to the sheath 3 on distal portions of the fingers 1A, 1B and are arranged to extend in channels and/or guides (not shown) to a control module 5. The control module 5 contains a power source, one or more actuators and control electronics for imparting a defined movement to the respective tendon 4 so as to move the fingers 1A, 1B into one or more predefined grips. The respective actuator may comprise an electric motor with one or more gears connected to a winding device, e.g. a cord reel, to which one or more of the tendons 4 is fastened. It is realized that, depending on implementation, the orthosis 2 may include one or more actuators for each finger and/or one actuator may be attached to a tendon 4 extending to two or more fingers. In the example of FIG. 1, three tendons 4 are attached to the thumb 1A and to a respective actuator (not shown) in the control module 5, where the actuators are operable to selectively pull the respective tendon 4 so as to impart a desired movement to the thumb 1A. The index finger 1B may be controlled into a bending motion by one tendon 4, shown in FIG. 1. Optionally, a further tendon (not shown) may be arranged on the rear side of the index finger 1B to impart a straightening motion to the finger 1B.

The control module 5 is arranged onto the forearm 6 of the individual by a band or strap 3B. As indicated by dashed lines, a set of bioelectric sensors 10 are arranged for contact with the forearm 6. Although four sensors 10 are shown in FIG. 1, any number of sensors 10 may be used. The bioelectric sensors 10 may be in the form of electrodes that are configured to detect the electrical activity produced by the skeletal muscles on the forearm 6 that are relevant for moving the fingers to be controlled by the orthosis 2. The sensors 10 may be arranged in contact with the skin or be implanted. In the following examples, the bioelectric sensors 10 are so-called EMG (electromyography) sensors and the bioelectric signals are EMG signals. In the illustrated example, the sensors 10 are integrated into the band 3B for application onto the skin of the forearm 6. It may be noted that the control module 5 may be arranged anywhere on the body of the individual and that the control module 5 may be physically separated into two or more devices, e.g. a power source, an actuator device and a control device (cf. 60 in FIG. 6). The sensors 10 may alternatively or additionally be arranged on the other forearm of the individual, thereby allowing the individual to control a hand orthosis 2 on the right hand 1 by muscle activity in the left forearm, or vice versa. In an alternative, the sensors 10 may be arranged to sense activity of muscles that are physically unrelated to the finger movement, and the orthosis 2 may be configured to move the fingers based on such muscle activity. For example, the orthosis 2 may attain one or more grips in dependence of the wrist angle.

Figure 2A:
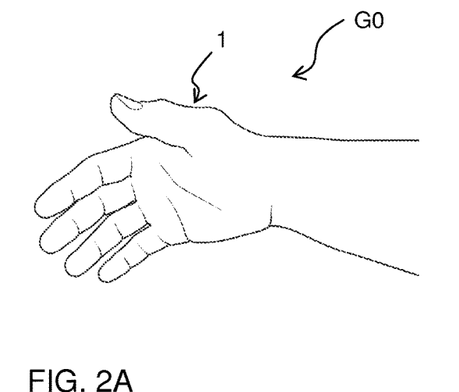
FIGS. 2A-2D illustrate examples of grips that may be attained by use of an active orthosis.
Figure 2B:
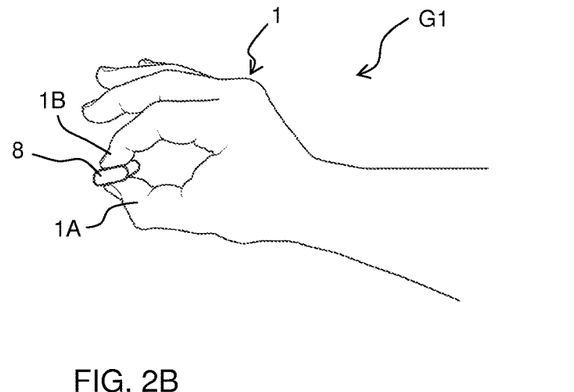
Figure 2C:
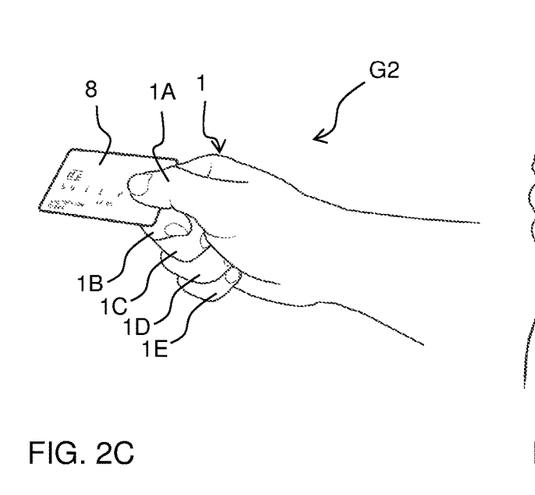
Figure 2D:
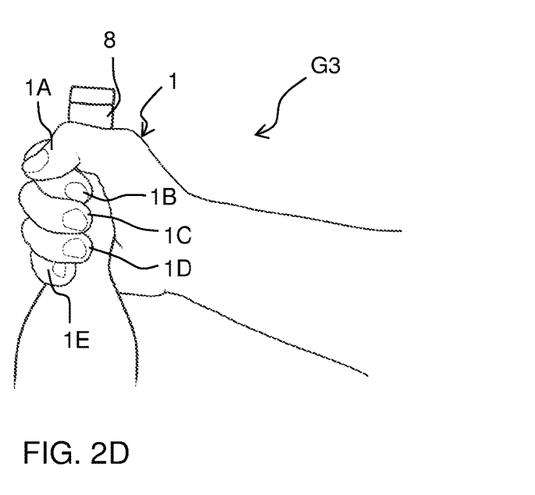

The orthosis 2 is operable, via the actuators, to attain different states, where each state corresponds to a predefined grip. As used herein, a "grip" not only includes activated grips in which one or more fingers 1A-1E are actively operated to apply a force onto an object, e.g. an external object or a body part, but also passive grips in which the fingers 1A-1E are relaxed and/or stationary and do not apply any force. The passive grip is thus an "open grip" or "relaxed grip". The arrangement of the fingers 1A-1E in the open grip may be left to the wearer, e.g. by decoupling the actuators so as to allow the wearer to attain any desired relaxed grip. Alternatively, the arrangement of the fingers 1A-1E in the relaxed grip may be set by the actuators and/or by the design of the sheath 3A. Examples of different grips are shown in FIGS. 2A-2D, where the orthosis has been omitted for clarity of presentation. FIG. 2A shows an open (relaxed) grip G0. FIG. 2B shows a pinch grip G1 in which the tips of the thumb 1A and the index finger 1B are moved into engagement with an object 8. FIG. 2C shows a lateral grip G3, in which at least the index finger 1B is bent and the tip of the thumb 1A is moved laterally and to engage an object 8 between the tip of the thumb 1 and the bent index finger 1B. FIG. 2D shows a cylindrical grip G4 in which one or more of the fingers 1A-1E are moved to press an object 8 onto the palm of the hand.

Embodiments of the invention involve a technique of operating an orthosis 2 to better mimic the movement of the fingers of a healthy individual when attaining different grips. One such embodiment involves determining, based on signals from the bioelectric sensors 10, an intended grip and an intended grip force for each finger 1A-1E involved in the intended grip. The intended grip may be determined among a set of predefined (predetermined) grips, e.g. as exemplified in FIGS. 2A-2D, where each predefined grip is associated with a predefined movement trajectory of the respective finger 1A-1E and thus activation of one or more selected actuators among the actuators in the orthosis 2. The intended grip force defines one or more set points for controlling the selected actuators based on an actual contact force of the respective finger 1A-1E involved in the intended grip. Thereby, it is possible to operate the selected actuators to achieve the intended grip with the intended grip force in a well-controlled and natural manner.

While the following description may refer to the orthosis 2 as shown in FIG. 1, the embodiments of the invention are not limited to any particular type of orthosis or structural configuration thereof.

Figure 3A:
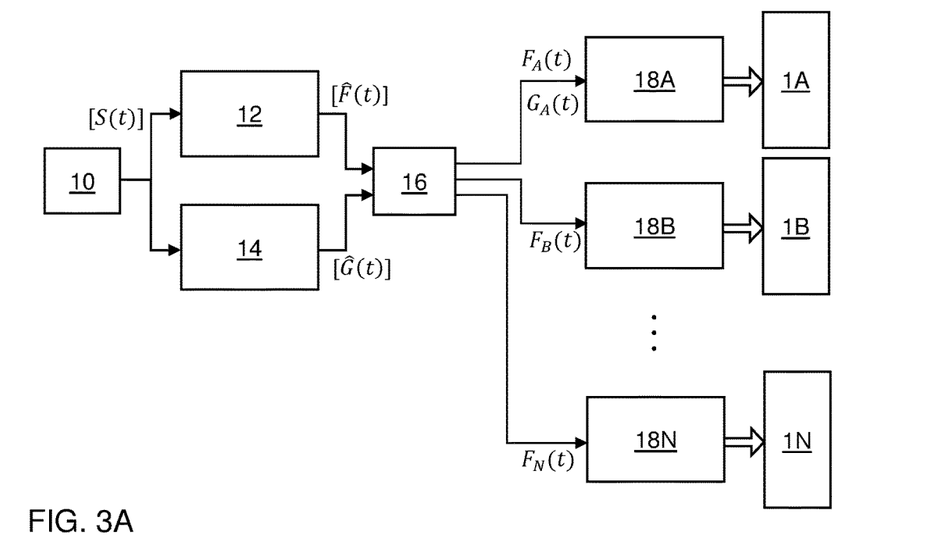
FIG. 3A is a block diagram of a control system of an active orthosis.

FIG. 3A is a block diagram of a control system of an orthosis attached to a number of limbs (fingers), which are schematically indicated and designated by 1A-1N. The control system operates on a set of EMG signals [S(t)] which are received from a set of EMG sensors 10 to selectively actuate one or more of the fingers 1A-1N. The control system includes a force prediction module 12, which is configured to process the EMG signals [S(t)] for determination of intended force data [PM] for the fingers 1A-1N. The intended force data [P(t)] may include an intended force value for each finger 1A-1N. The control system further includes a grip prediction module 14, which is configured to process the EMG signals [S(t)] for determination of intended grip data [Ĝ(t)] for the fingers 1A-1N. Depending on implementation, the grip data [Ĝ(t)] may include an index representing a selected grip, or a respective probability value for one or more candidate grips. A coordination module 16 operates on the intended force data [F̂(t)] and the grip data [Ĝ(t)] to generate intended force signals $F_A(t), \ldots, F_N(t)$ for finger controllers 18A-18N, which each comprise one or more actuators for moving the respective finger 1A-1N. The intended force signals $F_A(t), \ldots, F_N(t)$ are generated to cause the finger controllers 18A-18N to impart a desired movement of one or more of the fingers 1A-1N. To the extent that the one or more actuators of the respective finger controller 18A-18N are configured to impart a predefined two-dimensional (2D) finger movement, e.g. by bending the finger to move its distal portion in a 2D plane, the finger controller may operate solely on the intended force signal. If a finger controller has more than two degrees of freedom (DOF), e.g. by being operable to move a thumb in two or more directions with respect to the carpometacarpal (CMC) joint, the coordination module 16 may additionally provide a grip signal that indicates the intended grip and causes the finger controller to selectively operate its actuators in accordance with the intended grip. In FIG. 3A, such a grip signal $G_A(t)$ is provided by the coordination module 16 to the finger controller 18A.

The force prediction module 12 may be configured to evaluate (compute) one or more force-related parameters based on one or more of the EMG signals [S(t)] and determine the intended force data [F̂(t)] as a function thereof. Such force-related parameters may represent the time domain, the frequency domain or the time-frequency domain, or any combination thereof. Examples of force-related parameters include, without limitation, Wilson amplitude, variance, mean absolute value, waveform length, histogram, mean frequency, entropy, slope, etc. These and other potential force-related parameters are defined in the article "*Prediction of grasping force based on features of surface and intramuscular EMG*", by Mathiesen et al., published in 7th semester conference paper (2010) 1-9, and citations listed therein, all of which are incorporated herein by this reference. For example, the article indicates a linear relationship between Wilson amplitude and intended force.

The grip prediction module 14 may be configured to evaluate (compute) a plurality of grip-related signal features based on one or more of the EMG signals [S(t)] and operate a pattern recognition algorithm on the signal features to determine the grip data [Ĝ(t)], by assigning the signal features to one or more predefined classes that each represents an predefined grip. Such signal features are well-known in the art and may represent the time domain, the frequency domain or the time-frequency domain, or any combination thereof. Examples of signal features are given in the above-identified article by Mathiesen et al. The pattern recognition algorithm, if properly defined, ensures consistent and robust grip prediction. The pattern recognition algorithm may range in complexity from simple to advanced, e.g. depending on the number of sensors 10, the number of predefined grips, the number of fingers controlled by the orthosis, the degrees of freedom of the respective finger, etc. Examples of pattern recognition algorithms include, without limitation, a simple combination of evaluation rules, Bayes classifier, linear discriminant analysis (LDA), support vector machine (SVM), Gaussian mixture model (GMM), quadratic classifier, kernel density estimation, decision tree, artificial neural network (ANN), recurrent neural network (RNN), and Long Short Term Memory (LSTM). A more detailed example is given below with reference to FIG. 5.

Figure 3B:
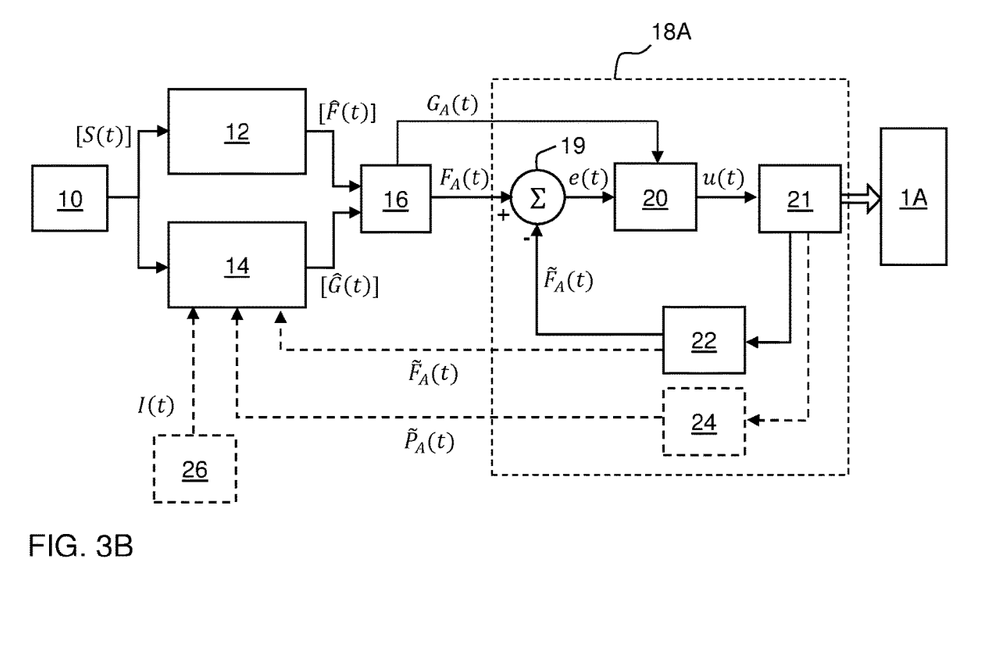
FIG. 3B is a detailed block diagram the control system of FIG. 3A for controlling a single finger.

In FIG. 3B, the structure of the finger controller 18A is shown in more detail, comprising a summation unit 19, an actuator controller 20 and an actuator 21. The summation unit 19 is configured to receive the intended force signal $F_A(t)$ from the coordination module 16 and a measured force signal $\tilde{F}_A(t)$ from a force sensing device 22, and output a difference or error signal e(t) corresponding to the momentary difference between the signals $F_A(t)$ and $\tilde{F}_A(t)$. The measured force signal $\tilde{F}_A(t)$ is a time sequence of actual force values, each representing a momentary application force (contact force) occurring between the finger 1A and an object which is touched or gripped by the finger 1A. The force sensing device 22 may be arranged in the sheath 3A (FIG. 1) or be attached to the finger 1A, e.g. in the form of a piezoelectric sensor, a force-sensing resistor (FSR), a load cell, etc. Alternatively, the force sensing device 22 may be included in or associated with the actuator 21 to indirectly measure the application force, e.g. by measuring a force applied to a tendon (4 in FIG. 1), a strain or torque on a drive axis, etc. In a further alternative, the force sensing device 22 may sense the orientation and/or position of one or more components of the actuator 21, e.g. the above-mentioned winding device, and algorithmically compute the applied force based thereon. The actuator controller 20 is configured to receive the error signal e(t) and generate a control signal u(t) for the actuator 21, which is arranged to impart a corresponding movement to the finger 1A. The finger controller 18 may include more than one actuator 21, and the actuator controller 20 may be configured to generate a respective control signal for each actuator 21 so as to minimize the error signal e(t). The actuator controller 20 may implement any available control algorithm, including proportional (P), integral (I) and derivative (D) control, or any combination thereof. In the example of FIG. 3B, the actuator controller 20 is also configured to receive the grip signal $G_A(t)$ from the coordination module 16. Based on the grip signal $G_A(t)$, the actuator controller 20 is operable to infer, by appropriate logic, which one(s) of the actuators 21 that should be actively controlled to form the intended grip.

FIG. 3B also indicates, by dashed arrows, that the grip prediction module 14 may be configured to receive the force signal $\tilde{F}_A(t)$ from the force sensing device 22, as well as a position signal $\tilde{P}_A(t)$ from a position sensing device 24. The position signal $\tilde{P}_A(t)$ is a time sequence of position values, each representing a momentary position of the finger 1A. In this context, a "position" refers to any metric or combination of metrics that defines the location of the finger or a part of the finger, e.g. a phalange, in relation to a predefined reference. The reference may, e.g., be a coordinate system, e.g. Cartesian, polar, cylindrical or spherical, with a predefined location on the hand 1 or the orthosis 2. In one example, the position sensing device 24 is configured to algorithmically compute the position based on the current orientation or position of one or more components of the actuator 21 and/or based on signal(s) from one or more inertial sensors on the finger 1A, e.g. arranged in the sheath 3A.

FIG. 3B further indicates, by a dashed arrow, that the grip prediction module 14 may be configured to receive one or more inertial signals I(t) from one or more inertial sensors 26, e.g. comprising one or more accelerometers and/or gyroscopes. The inertial signal(s) I(t) may be indicative of one or more of acceleration, angular velocity, orientation, etc. The inertial sensor(s) 26 may be arranged in one or more finger controllers 18A-18N, and/or on one or more fingers 1A-1N, the hand 1, the sheath 3A, or elsewhere on the wearer of the orthosis 2.

The finger controllers 18B-18N in FIG. 3A may be configured in correspondence with the finger controller 18A as described above.

Figure 4:
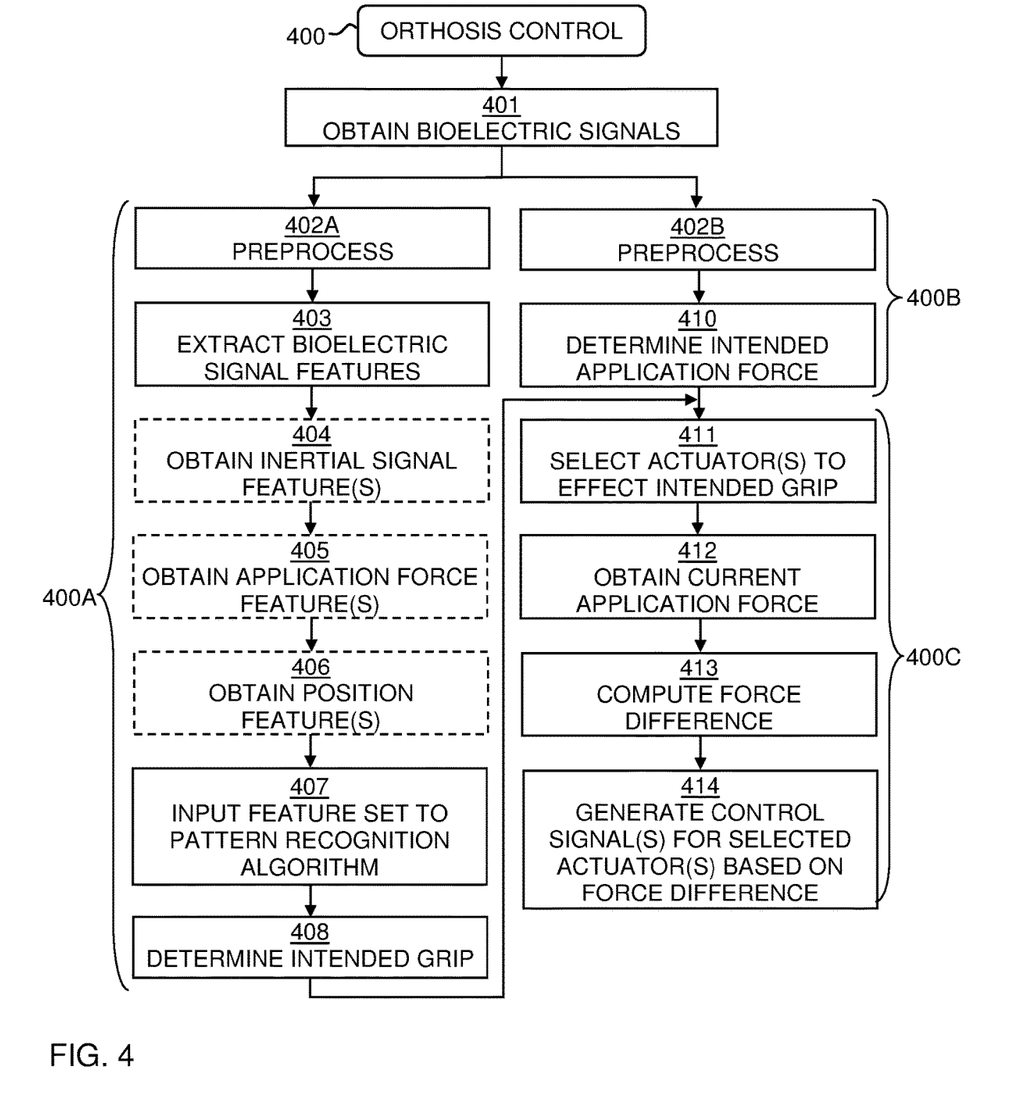
FIG. 4 is a flow chart of a method for controlling an active orthosis.

FIG. 4 shows an embodiment of a method 400 for controlling an orthosis. The method 400 will be exemplified with reference to the control system in FIGS. 3A-3B for the hand orthosis 2 in FIG. 1. In the illustrated embodiment, the method 400 is divided into three sub-sequences 400A, 400B and 400C. Sub-sequence 400A predicts the intended grip and is performed by module 14. Sub-sequence 400B predicts the intended force and is performed by module 12. Sub-sequence 400C selects the actuators in the orthosis to be operated and controls the selected actuators to perform the intended grip. Sub-sequence 400C may be performed by module 16 and the finger controllers 18A-18N. The method 400 may be repeatedly executed at consecutive time steps, although the time steps may differ between the sub-sequences 400A-400C.

In step 401, EMG signals [S(t)] are obtained from the EMG sensors 10. The EMG signals [S(t)], or a respective subset thereof, are processed by sub-sequence 400A and sub-sequence 400B. In sub-sequence 400A, one or more EMG signals [S(t)] are pre-processed (step 402A), e.g. by amplification, filtering for noise reduction, normalization and rectification, as is well-known in the art. In step 403, a plurality of EMG signal features are extracted within a time window in the pre-processed EMG signal(s), e.g. as exemplified above with reference to module 14. Steps 404-406 are optional and may be included to improve the prediction of the intended grip. In step 404, one or more inertial signal features are extracted from the inertial signal(s) I(t). The inertial signal feature(s) may represent any type of inertial parameter, including without limitation linear acceleration in one or more directions, linear velocity in one or more directions, one or more orientation angles, angular velocity in one or more directions, angular acceleration in one or more directions, etc. In step 405, one or more force features are extracted from the measured force signal for the respective finger (cf. $\tilde{F}_A(t)$ in FIG. 3B). The force feature(s) may include an individual force value, a time average of force values, a maximum or minimum force value within a time window, a slope, a variance, etc. In step 406, one or more position features are extracted from the measured position signal for the respective finger (cf. $\tilde{P}_A(t)$ in FIG. 3B). The position feature(s) may include an individual position value, a time average of position values, a maximum or minimum position value within a time window, a slope, a variance, etc. In step 407, the features obtained by steps 403-406 are provided as input values (also denoted "feature set" herein)

to a pattern recognition algorithm, which may be of any type, e.g. as exemplified above with reference to module 14. In step 407, the pattern recognition algorithm outputs the grip data [G(t)] (FIGS. 3A-3B), which is used by step 408 for determining the intended grip. If the grip data [G(t)] comprises probabilities for different predefined grips (candidate grips), step 408 may select the grip with the highest probability. In a variant (not shown), step 408 may determine the intended grip based on a combination of the grip data [G(t)] and the intended force data [F(t)], which is determined by step 410 (below).

Figure 5:
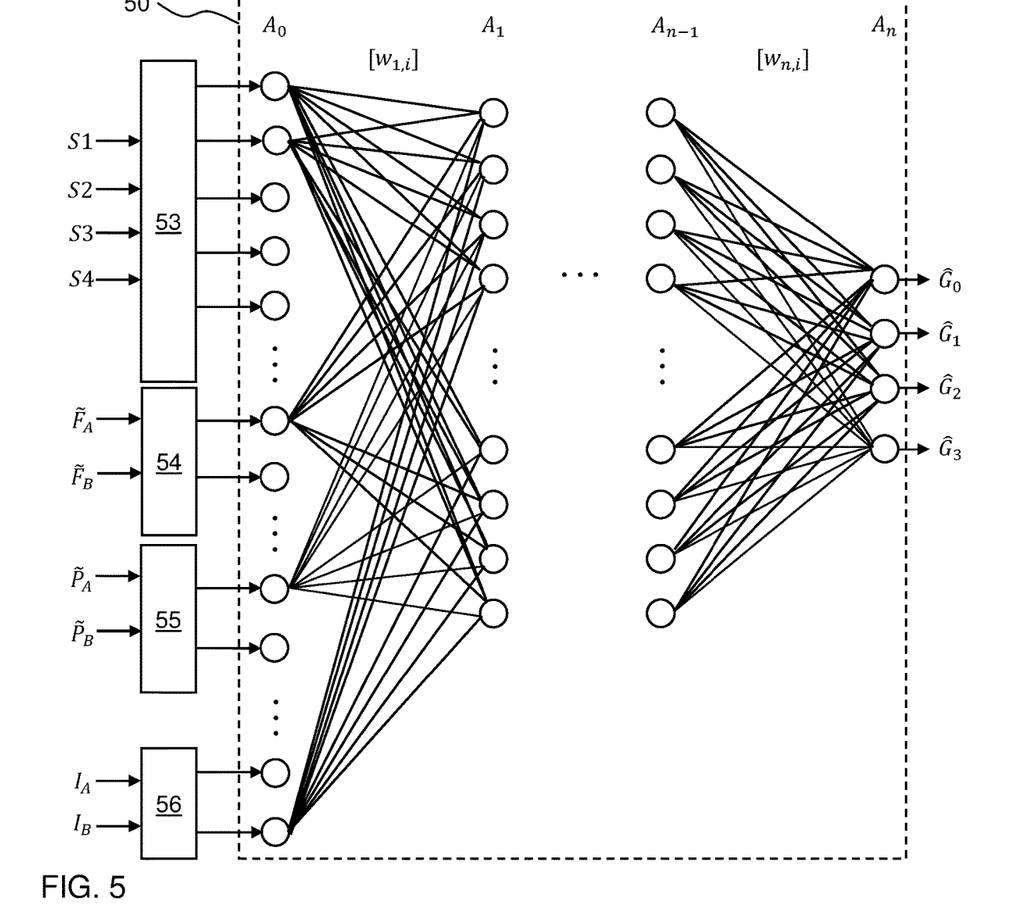
FIG. 5 is a schematic view of an artificial neural network for determining an intended grip of a human subject wearing an active orthosis.

FIG. 5 shows an example of a pattern recognition device 50, which may be used in step 407 and may be part of the grip prediction module 14 in FIGS. 3A-3B. In the illustrated example, the pattern recognition device 50 comprises an artificial neural network (ANN), which has been trained to classify incoming feature sets into four candidate grips, designated by $\hat{G}_0$-$\hat{G}_3$, e.g. corresponding to grips G0-G3 in FIGS. 2A-2D. Depending on implementation, the ANN 50 may indicate a single predicted grip among $\hat{G}_0$-$\hat{G}_3$ for each feature set, or a probability value for each of $\hat{G}_0$-$\hat{G}_3$. ANNs are well-known as such will not be described in detail. It may be noted that the ANN 50 may have any number of hidden layers intermediate the input layer $A_0$ and the output layer $A_n$. Further, each neuron (represented by a circle in FIG. 5) is assigned a respective weight and optionally a respective bias, and FIG. 5 collectively designates the weights applied by the neurons in layer $A_1$ by $[w_{1,i}]$ and in layer $A_n$ by $[w_{n,i}]$. Any conventional activation function may be used for the respective layer. Although not shown in FIG. 5, all neurons in the respective layer are connected to all neurons in the adjacent layer(s). FIG. 5 also illustrates feature extraction modules 53-56 for extracting features in accordance with the respective step 403-406. In the illustrated example, pre-processed EMG signals S1-S4 are processed by module 53 to provide a set of EMG features to the ANN 50, measured force signals $\tilde{F}_A$, $\tilde{F}_B$ for fingers 1A, 1B are processed by module 54 to provide a set of force features to the ANN 50, measured position signals $\tilde{P}_A$, $\tilde{P}_B$ for fingers 1A, 1B are processed by module 55 to provide a set of position features to the ANN 50, and inertial signals $I_A$, $I_B$ for fingers 1A, 1B are processed by module 56 to provide a set of inertial features to the ANN 50. In a conventional implementation, the feature set only includes EMG signal features. By insightful reasoning, the present inventors have found that improved grip prediction, e.g. with respect to robustness and accuracy of prediction, may be achieved by expanding the feature set to include force feature(s), position feature(s) or inertial feature(s), or any combination thereof. It is realized that the values of the force features, position features and inertial features may differ between different grips and thus enable an improved classification of the feature set into an intended grip. The expanded feature set is applicable to all types of pattern recognition algorithms, not only ANNs.

The inventors have further found that by including the relaxed grip $\hat{G}_0$ among the candidate grips, irrespective of pattern recognition algorithm, the user is able to control the orthosis 2 to release an active grip in a natural and intuitive way.

Reverting to sub-sequence 400B in FIG. 4, one or more EMG signals [S(t)] are pre-processed (in step 402B), e.g. by amplification and filtering for noise reduction. In step 410, an intended force for each finger is computed for signal values within a time window of the pre-processed EMG signal(s), e.g. as exemplified above with reference to module 12. Thus, step 410 results in intended force data [F(t)].

In sub-sequence 400C, step 411 selects the actuators that should be operated to perform the intended grip. Step 411 may be omitted if all actuators of a finger controller are operated for all of the predefined grips. Step 412 obtains a current value of the actual application force for the respective finger that is involved in the intended grip. As understood from the foregoing, step 412 may obtain the current value from the respective measured force signal (cf. $\tilde{F}_A$(t) in FIG. 3B). The current value may be a single force value or a time-average of force values in the measured force signal. In step 413, a difference value (momentary force difference) between the intended force and the current value is computed. The difference value forms a signal value in the error signal e(t) in FIG. 3B. In step 414, a control value is generated for the respective selected actuator in accordance with a predefined control algorithm and as a function of the difference value. The control value forms a signal value in the control signal u(t) in FIG. 3B.

It is realized that the method 400 is repeatedly executed to progressively move the fingers into the intended grip. The grip prediction by sub-sequence 400A and the force prediction by sub-sequence 400B may but need not be performed concurrently. It should also be understood that the orthosis 2 may configured to allow the wearer to move its fingers, assuming that the wearer has such ability, without resistance from the actuators. For example, the orthosis may be a handgrip strengthener, which allows the wearer to move its fingers towards or into the intended grip, and the orthosis strengthens the intended grip in accordance with the intended force. Thus, the force-based movement control as described in the foregoing may be performed only during part of the movement into the intended grip. In another example, if an intended non-relaxed grip is detected but no intended force, the orthosis may nevertheless move the fingers towards the intended grip, e.g. by the coordination module 16 generating the intended force signals $F_A(t), \ldots, F_M(t)$ with predefined values. If an intended force is detected during the movement, the coordination module 16 may switch to generating the intended force signals $F_A(t), \ldots, F_M(t)$ to reflect the intended force, so as to achieve the intended grip with the intended force. It is also conceivable that the grip prediction by sub-sequence 400A is omitted, e.g. if the orthosis is configured to perform a single grip.

It is realized that if the momentary position of the respective finger is measured (cf. $\tilde{P}_A$(t) in FIG. 3B) while the wearer starts to move its fingers, one or more measured positions of the respective finger may be analyzed to validate the output of the pattern recognition algorithm. Such a validation is effectively embedded into the pattern recognition algorithm when one or more position features are included in the feature set (cf. step 406 and FIG. 5). Alternatively or additionally, the method 400 may comprise a step of matching the measured position(s) to the output of the pattern recognition algorithm and refraining from proceeding to sub-sequence 400C if there is a mismatch between the measured position(s) and the movement trajectories of the grip that is predicted by the pattern recognition algorithm. In a further alternative, one or more of the weight factors of the ANN 50 may be modified as function of the measured positions (cf. $\tilde{P}_A$, $\tilde{P}_B$). In one such embodiment, the method 400 comprises a step of modifying one or more of the weight factors $[w_{n,i}]$ of the output layer $A_n$ based on the momentary finger position, so as to drive the prediction of the ANN 50 towards the intended grip with the movement trajectories that match the measured position signals.

The bioelectric signals are typically weak and noisy and thereby susceptible to disturbances. For example, sudden movements of the body or a body part of the wearer may distort the bioelectric signals [S(t)] and disturb the operation of the orthosis. In some embodiments, the method 400 may include a step of processing the inertial signal(s) I(t) for detection of a disturbance condition, e.g. a sudden change in velocity, position or orientation, and step of disabling at least step 414 if the disturbance condition is detected. In one example, the detection of a disturbance condition may cause the operation of the orthosis 2 to be temporarily suspended. In another example, step 414 may be replaced with a step of using the latest intended force signals $F_A(t), \ldots, F_N(t)$ until the disturbance has subsided or for a predefined time period, so that the operation of the orthosis 2 continues in a safe way during the disturbance.

To further exemplify embodiments of the invention, reference is made to FIGS. 2A-2D. In the following examples, it is assumed that the orthosis 2 is configured, by the respective finger controller 18A-18E, to move the fingers 1B-1E along a respective default trajectory, i.e. in a predefined 2D movement, and to move the thumb 1A along three different movement trajectories. If the control system detects that the wearer intends to attain the pinch grip G1 with a first force, the orthosis operates selected actuators to move the thumb 1A on a first trajectory associated with the pinch grip G1 and the index finger 1B on its default trajectory, until the first force is measured for the thumb 1A and the index finger 1B. If the control system then detects that wearer intends to attain the relaxed grip G0, the orthosis may either disengage the actuators to allow the wearer to move the fingers into the relaxed grip G0 or operate the selected actuator to move the fingers into the relaxed grip G0. If the control system detects that the wearer intends to attain the lateral grip G2 with a first force for the thumb 1A and a second force for the other fingers 1B-1E, the orthosis operates selected actuators to move the fingers 1B-1E on their respective default trajectory and the thumb 1A on a second trajectory associated with the lateral grip G2, until the first force is measured for the thumb 1A and the second force is measured for the fingers 1B-1E. If the control system detects that the wearer intends to attain the cylindrical grip G3 with a first force for all fingers 1A-1E, the orthosis operates selected actuators to move the fingers 1B-1E on their respective default trajectory and the thumb 1A on a third trajectory associated with the cylindrical grip G3, until the first force is measured for all fingers 1A-1E.

Figure 6:
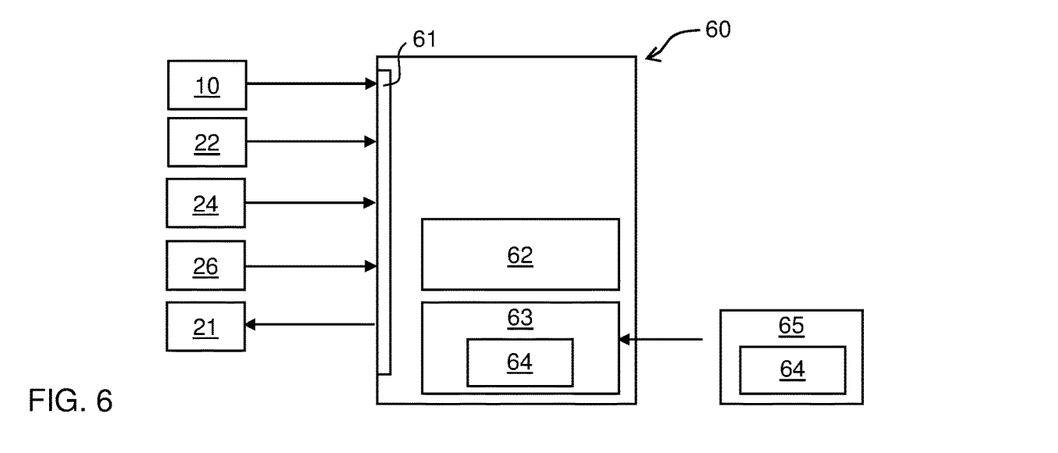
FIG. 6 is a block diagram of a control device for operating an active orthosis.

FIG. 6 is a diagrammatic representation of a control device 60 in accordance with an embodiment of the invention. The device 60 comprises a communication module 61 defining one or more interfaces for data communication in accordance with any suitable protocol or protocols. As shown, the device 60 may input data from bioelectric sensor(s) 10, force sensing device(s) 22, position sensing device(s) 24, inertial sensor(s) 26, and output control signal(s) for actuator(s) 21, via the communication module 61. The device 60 further comprises one or more processors 62, e.g. a central processing unit (CPU), a microprocessor, a microcontroller, a digital signal processor (DSP), an application specific integrated circuit (ASIC), a field programmable gate array (FPGA), or any combination thereof. The device 60 further comprises system memory 63, which may include computer memory in the form of volatile and/or non-volatile memory such as read only memory (ROM), random access memory (RAM) and flash memory. The memory 63 may store computer instructions 64 (e.g. software or program code) for causing the device 60 to perform any one of the methodologies discussed herein. The instructions 64 may be supplied to the device 60 on a computer-readable medium 65, which may be a tangible (non-transitory) product (e.g. magnetic medium, optical medium, read-only memory, flash memory, digital tape, etc) or a propagating signal. When executed by the processor(s) 62, the instructions 64 may cause the processor(s) 62 to perform any one of the methodologies discussed herein. In this context, it is to be understood that any of the modules 12, 14, 16, 18A-18E described in the foregoing may be implemented by the processor(s) 62 executing the instructions 64. However, it is also conceivable that one or more of the modules 12, 14, 16, 18A-18E are implemented solely by dedicated hardware.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A method of controlling an active orthotic device attached to a human subject to facilitate movement of a body part that is connected to a joint of the human subject, the active orthotic device comprising an actuator that moves the body part about the corresponding joint and into contact with a target object so that body part engages the target object, wherein the target object is different than any part of the active orthotic device, the method comprising:
   obtaining one or more bioelectric signals from one or more bioelectric sensors attached to or implanted in the human subject,
   processing the one or more bioelectric signals and predicting an intended application force of the body part against the target object,
   obtaining a force feedback signal from a force sensing device, the force feedback signal representing an amount of force applied by the body part on the target object,
   determining an intended movement of the body part with respect to the target object, and
   generating control signals for the actuator as a function of a momentary difference between the intended application force and the applied force and as a function of the intended movement of the body part,
   wherein the determining the intended movement of the body part comprises:
   extracting signal features from the one or more bioelectric signals,
   extracting signals features from the force feedback signal, and
   operating a pattern recognition algorithm on input values, the input values comprising the signal features extracted from the one or more bioelectric signals and the signal features extracted from the force feedback signal, to cause the pattern recognition algorithm to process the input values and determine the intended movement of the body part.

2. The method of claim 1, wherein the actuator is one of a set of actuators and the method further comprises identifying one or more selected actuators from the set of actuators that require actuation to effectuate the intended movement of the body part, and generating a respective set of control signals for each of the one or more selected actuators.

3. The method of claim 2, wherein the respective set of control signals is generated to cause the body part to perform the intended movement of the body part and apply the intended application force against the target object.

4. The method of claim 1, wherein the intended movement of the body part is selected from at least two predefined body part movements, each of the predefined body part movements corresponding to a predefined movement trajectory of the body part.

5. The method of claim 4, wherein one of the predefined body part movements corresponds to the body part being one of a relaxed state or a stationary state.

6. The method of claim 1, wherein the intended movement of the body part is determined collectively for two or more body parts of the human subject.

7. The method of claim 1, wherein the pattern recognition algorithm outputs at least one candidate movement for the body part and the determining of the intended movement of the body part further comprises validating the at least one candidate movement for the body part against a position signal representing an actual movement of the body part.

8. The method of claim 1, further comprising: obtaining an inertial signal from an inertial sensor in the active orthotic device or on the human subject, determining an inertial value from the inertial signal, and providing the inertial value as a further input value for the pattern recognition algorithm.

9. The method of claim 1, further comprising: obtaining a position signal from a position sensing device associated with the actuator or the body part, determining a position value from the position signal, the position value being indicative of a momentary position of the body part, and providing the position value as a further input value for the pattern recognition algorithm.

10. The method of claim 1, wherein the pattern recognition algorithm comprises an artificial neural network that trained to process the input values for determination of the intended movement of the body part.

11. The method of claim 10, wherein the artificial neural network has an output layer configured to provide output data indicative of the intended movement of the body part, and the method further comprising: obtaining a position signal representing actual movement of the body part, and modifying one or more weight factors of the output layer as a function of the position signal.

12. The method of claim 1, wherein the body part is a finger on a hand of the human subject.

13. The method of claim 1, wherein the body part is a finger on a hand of the human subject, and the intended movement of the body part is an intended grip action by one or more fingers on the hand.

14. The method of claim 1, further comprising: obtaining an inertial signal from an inertial sensor in the active orthotic device or on the human subject, processing the inertial signal for detection of a disturbance condition, and, upon detection of the disturbance condition, temporarily disabling the generating of the of control signals.

15. A non-transitory computer-readable medium storing computer instructions which, when executed by a processor, cause the processor to perform the method of claim 1.

16. A control device for an active orthotic device attached to a human subject to facilitate movement of a body part that is connected to a joint of the human subject, the active orthotic device having an actuator that moves the body part about the corresponding joint and into contact with a target object so that body part engages the target object, wherein the target object is different than any part of the active orthotic device, the control device configured to:
  obtain one or more bioelectric signals from one or more bioelectric sensors attached to or implanted in the human subject,
  process the one or more bioelectric signals and predict an intended application force of the body part against the target object,
  obtain a force feedback signal from a force sensing device, the force feedback signal representing an amount of force applied by the body part on the target object,
  determine an intended movement of the body part with respect to the target object, and
  generate control signals for the actuator as a function of a momentary difference between the intended application force and the applied force and as a function of the intended movement of the body part,
  wherein the control device is further configured to determine the intended movement of the body part by:
    extracting signal features from the one or more bioelectric signals,
    extracting signals features from the force feedback signal, and
    operating a pattern recognition algorithm on input values, the input values comprising the signal features extracted from the one or more bioelectric signals and the signal features extracted from the force feedback signal, to cause the pattern recognition algorithm to process the input values and determine the intended movement of the body part.

17. An active orthotic device configured to be attached to at least one body part a human subject, the active orthotic device comprising:
  an actuator that moves the body part about the corresponding joint and into contact with a target object so that body part engages the target object, wherein the target object is different than any part of the active orthotic device, and
  the control device according to claim 16.

* * * * *